(12) United States Patent
Bakkenes et al.

(10) Patent No.: US 8,759,574 B2
(45) Date of Patent: Jun. 24, 2014

(54) PROCESS FOR THE PREPARATION OF A COMPOSITION COMPRISING MESO-TARTARIC ACID

(75) Inventors: Hendrikus Wilhelmus Bakkenes, Apeldoorn (NL); Roberto Aloysius Gerardus Maria Bergevoet, Beek (NL); Johannes Albertus Maria Meijer, Schalkhaar (NL); Maria Steensma, Arnhem (NL)

(73) Assignee: Akzo Nobel Chemicals International B.V., Amersfoort (NL)

( * ) Notice: Subject to any disclaimer, the term of this patent is extended or adjusted under 35 U.S.C. 154(b) by 76 days.

(21) Appl. No.: 13/322,319

(22) PCT Filed: May 27, 2010

(86) PCT No.: PCT/EP2010/057287
§ 371 (c)(1),
(2), (4) Date: Feb. 8, 2012

(87) PCT Pub. No.: WO2010/139588
PCT Pub. Date: Dec. 9, 2010

(65) Prior Publication Data
US 2012/0130124 A1    May 24, 2012

Related U.S. Application Data

(60) Provisional application No. 61/183,269, filed on Jun. 2, 2009.

(30) Foreign Application Priority Data

Jun. 2, 2009  (EP) .................................... 09161723

(51) Int. Cl.
*C07C 59/225*    (2006.01)
(52) U.S. Cl.
USPC ........................................................ 562/585
(58) Field of Classification Search
CPC .. C07C 51/412; C07C 51/487; C07C 59/255; C01D 3/26; C07B 2200/13; G03G 15/00; G03G 21/1619
USPC .......... 562/591, 590, 579, 582, 512, 401, 585
See application file for complete search history.

(56) References Cited

U.S. PATENT DOCUMENTS

| | | | |
|---|---|---|---|
| 2,257,284 A | 9/1941 | Stokes et al. | |
| 2,947,665 A | 8/1960 | Foster | |
| 3,953,504 A | 4/1976 | Saotome et al. | |
| 3,998,878 A | 12/1976 | Hearon et al. | |
| 4,016,207 A | 4/1977 | Hearon et al. | |
| 4,048,225 A | 9/1977 | Prescher et al. | |
| 4,150,241 A | 4/1979 | Prescher et al. | |
| 4,705,876 A | 11/1987 | Ivanov et al. | |

FOREIGN PATENT DOCUMENTS

| | | |
|---|---|---|
| FR | 2309505 | 9/1976 |
| JP | 51-098215 | 8/1976 |
| JP | 51-108017 | 9/1976 |
| JP | 2004-123685 | 4/2004 |
| NL | 7600872 | 8/1976 |
| WO | 00/59828 | 10/2000 |
| WO | WO 00 59828 | * 10/2000 |

OTHER PUBLICATIONS

International Search Report for PCT/EP2010/057287, dated Jul. 21, 2010, 3 pages.
Krist. Strukt. Neorg. Soedin., 1974, pp. 103-126, manual translation of the conclusion (no English translation provided).
Kroon, J., et al., "The Crystal Structures of Potassium Mesotartrate Dihydrate and the Isomorphous Rubidium Salt", Acta Cryst., 1965, vol. 19, pp. 293-297.
Kam, Kinson C., et al., "Chemical and Structural Diversity in Chiral Magnesium Tartrates and their Racemic and *Meso* Analogues", Crystal Growth & Design, 2007, vol. 7, No. 8, pp. 1522-1532.

* cited by examiner

*Primary Examiner* — Brandon Fetterolf
*Assistant Examiner* — Blaine G Doletski
(74) *Attorney, Agent, or Firm* — Kenyon & Kenyon LLP

(57) ABSTRACT

The present invention relates to a process for the preparation of a composition comprising tartaric acid wherein between 55 and 90% by weight of the tartaric acid is meso-tartaric acid, comprising the steps of (i) preparing an aqueous mixture comprising between 35 and 65% by weight of a di-alkali metal salt of L-tartaric acid, a di-alkali metal salt of D-tartaric acid, a mixture of di-alkali metal salts of L-tartaric acid, D-tartaric acid, and optionally meso-tartaric acid, and between 2 and 15% by weight of an alkali metal or alkaline metal hydroxide, and (ii) stirring and heating the aqueous mixture to a temperature of between 100° C. and its boiling point until between 55 and 90% by weight of tartaric acid has been converted to meso-tartaric acid.

21 Claims, 1 Drawing Sheet

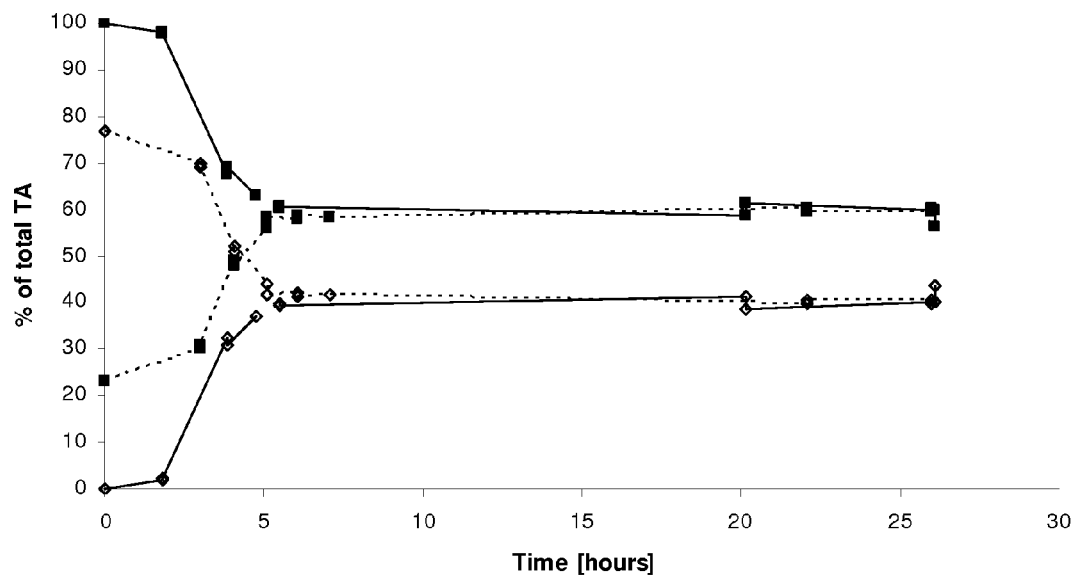
Figure 1: Relative conversion in time of comparative examples A(i) and A(ii)
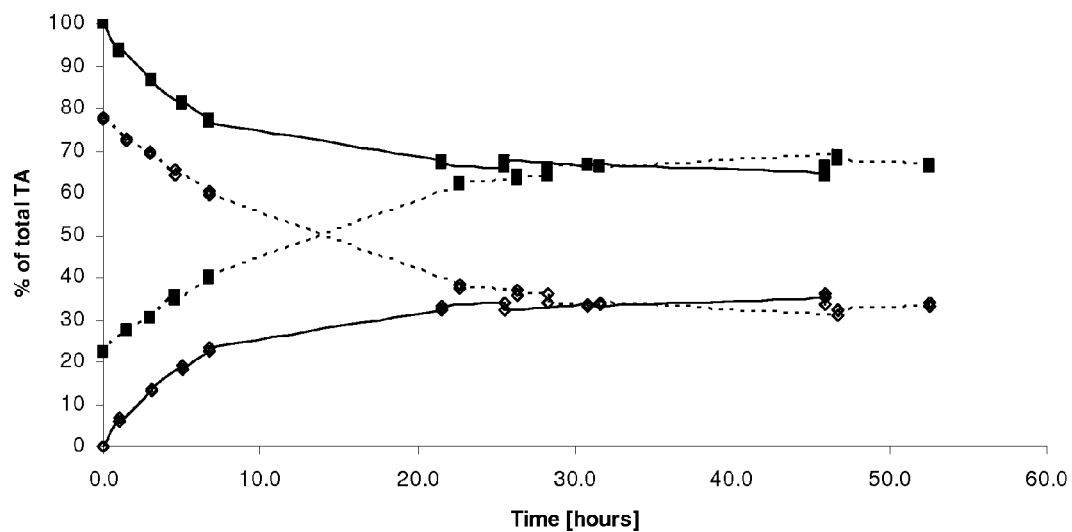
Figure 2: Relative conversion in time of comparative examples B(i) and B(ii)

US 8,759,574 B2

PROCESS FOR THE PREPARATION OF A COMPOSITION COMPRISING MESO-TARTARIC ACID

REFERENCE TO RELATED APPLICATIONS

This application is the U.S. National Phase of PCT/EP2010/057287 filed on May 27, 2010, and claims the benefit of US Provisional Application No. 61/183,269, filed on Jun. 2, 2009.

FIELD OF INVENTION

The present invention relates to a process for the preparation of a composition comprising tartaric acid wherein between 55 and 90% by weight of the tartaric acid is the meso isomer. Furthermore, it relates to the use of this composition for the preparation of a non-caking additive for sodium chloride or potassium chloride.

BACKGROUND

Sodium chloride tends to form large, agglomerated masses upon exposure to moisture, particularly during long periods of storage. These hardened masses are generally referred to as cakes. A non-caking agent is often added to the salt to prevent the formation of cakes. In recent years much effort has been put into the development of improved non-caking salt agents which are inexpensive and environmentally safe, and which are effective in small amounts. The iron complex of a mixture of tartaric acids comprising meso-tartaric acid was found to be an effective non-caking additive for sodium chloride. Particularly preferred is a non-caking additive comprising an iron complex of a mixture of tartaric acids, with between 55 and 90% by weight, more preferably with between 60 and 80% by weight, thereof being meso-tartaric acid.

Several stereoselective synthetic routes towards pure meso-tartaric acid exist. However, these methods are either not economically attractive or undesired byproducts are formed. For instance, it was found that epoxidation of fumaric acid with concentrated $H_2O_2$ followed by hydrolysis leads to formation of only the meso-isomer of tartaric acid, without the use of any metal salts. However, relatively harsh process conditions, low conversion and byproduct formation make this route not very attractive. Furthermore, it has been found that maleic acid can be converted into meso-tartaric acid in presence of $KMnO_4$. The main drawback of this route is the stoichiometric consumption of $KMnO_4$ and the need to separate the meso-tartaric acid out of the meso-tartaric acid manganese salt—for application as non-caking additive on sodium chloride the meso-tartaric acid has to be virtually Mn-free. Along the same lines, Mn/Amine complex as catalyst or oxidizing agent and optionally $H_2O_2$ may be used to convert maleic acid into meso-tartaric acid, but such routes have similar product purification challenges.

WO 00/59828 discloses in the Examples a method for producing a mixture of tartaric acids which includes meso-tartaric acid. It mentions that it can be prepared by treating a natural or synthetic tartaric acid (CAS registry numbers 87-69-4 and 147-71-7, respectively) solution with concentrated NaOH at temperatures above 100° C. Part of the L-, D- and/or DL-tartaric acid is then converted to the desired meso-tartaric acid (CAS registry number 147-73-9). However, it was found that by following this procedure, it is merely possible to prepare tartaric acid mixtures with up to a maximum of 50% by weight of the tartaric acid being the meso isomer.

Until now, however, no easy and economically attractive processes existed for the preparation of mixtures of tartaric acid comprising over 50% by weight of meso-tartartic acid.

SUMMARY OF THE INVENTION

It is an object of the present invention to provide an economically attractive method for the preparation of a composition comprising tartaric acids with between 55 and 90% by weight thereof, preferably between 60 and 80% by weight thereof, being meso-tartaric acid, and which method does not have the drawback of undesired byproduct formation.

The objective has been met with the following preparation method. Said method comprises the following steps: (i) preparing an aqueous mixture comprising between 35 and 65% by weight, preferably between 40 and 60% by weight, of a di-alkali metal salt of L-tartaric acid, a di-alkali metal salt of D-tartaric acid, a mixture of di-alkali metal salts of L-tartaric acid, D-tartaric acid, and optionally meso-tartaric acid, and between 2 and 15% by weight, preferably between 4 and 10% by weight, of an alkali metal or alkaline metal hydroxide, and (ii) stirring and heating the aqueous mixture to a temperature of between 100° C. and its boiling point until between 55 and 90% by weight of tartaric acid, preferably between 60 and 80% by weight of tartaric acid, has been converted to meso-tartaric acid. Preferably, the aqueous mixture is subsequently cooled, preferably to a temperature of 90° C. or lower, more preferably to a temperature of 70° C. or lower, or for example to room temperature, to obtain an aqueous slurry comprising a mixture of tartaric acids of which between 55 and 90% by weight is meso-tartaric acid.

BRIEF DESCRIPTION OF DRAWINGS

FIG. 1 shows the relative conversion of time of comparative examples A(i) and A(ii).

FIG. 2 shows the relative conversion of time of comparative examples B(i) and B(ii).

DETAILED DESCRIPTION OF INVENTION

Other than in the operating examples, or where otherwise indicated, all numbers expressing quantities of ingredients, reaction conditions, and so forth used in the specification and claims are to be understood as being modified in all instances by the term "about".

It was found that with this process, either from the start of the process (i.e. in step (i)) or during step (ii), the solubility limit of meso-tartaric acid will be exceeded, which will result in meso-tartaric acid precipitating from the reaction mixture. Accordingly, the term "aqueous mixture" as used throughout the description is used in relation to clear aqueous solutions, but also in relation to water-based slurries.

The alkali metal in the di-alkali metal salts of the tartaric acids used as starting material in the process according to the present invention preferably comprises sodium. The alkali metal or alkaline metal hydroxide used in this process preferably comprises sodium hydroxide.

L(+)-tartaric acid disodium salt, also denoted as bisodium L-tartrate, is commercially available, e.g. from Sigma-Aldrich (CAS Number 6106-24-7). It is noted that instead of L(+)-tartaric acid disodium salt, it is also possible to use L(+)-tartaric acid (commercially available from e.g. Sigma-Aldrich, CAS Number 87-69-4), and prepare the L(+)-tartaric acid disodium salt in situ, by addition of additional NaOH. The same holds for the other potential starting material, DL-tartaric acid disodium salt: it may be purchased from e.g.

Sigma-Aldrich or produced in situ from DL-tartaric acid (CAS Number 133-37-9) or DL-tartaric acid monosodium salt and NaOH. In fact any tartaric acid source, containing D, L, meso in any proportion and in the acidic or salt form can be used for this process. D-tartaric acid can also be used as starting material, but this is less preferred because it is relatively expensive. The use of L-tartaric acid disodium salt (either produced in situ by addition of NaOH or used as such) is preferred because these starting materials are relatively cheap and the process to prepare a composition with between 55 and 90% by weight of meso-tartaric acid is faster than when a mixture of D- and L-tartaric acid is used as starting material. Obviously, it is also possible to use a mixture of D-, L-, and meso-tartaric acid, with the amount of meso-tartaric acid being less than 50% by weight of the total weight of the tartaric acids.

The process is preferably carried out at atmospheric pressure. However, it is also possible to perform the process at elevated pressure, e.g. 2-3 bar, but this is less preferred.

It is noted that the period of time the mixture needs to be stirred and heated (i.e. step (ii) of the preparation process) to obtain the desired amount of meso-tartaric acid is dependent on the concentration of tartaric acid in the aqueous mixture, the amount of alkali or alkaline metal hydroxide present, the temperature and pressure. Typically, however, in step (ii) the mixture is stirred and heated for between 3 and 200 hours, if the process is performed at atmospheric pressure.

The amount of meso-tartaric acid in the mixture in step (ii) can be determined by conventional methods, such as by $^1$H-NMR (e.g. in $D_2O$/KOH solution using methanesulphonic acid as internal standard). The NMR-spectrum of meso-tartaric acid is slightly different from the NMR-spectrum of DL-tartaric acid. NMR is used to determine the meso-tartaric acid:DL-tartaric acid ratio in a reaction sample or optionally to quantify the DL or meso isomer concentration by using an internal or external standard. D- and L-tartaric acid cannot be distinguished by NMR directly. To determine the concentrations of D, L and meso-tartaric acid, chiral HPLC is a suitable method.

As the skilled person will recognize, depending on the pH value, tartaric acid is present in an aqueous solution in the carboxylic acid form or in the form of a salt (bitartrate or tartrate). For example, it is present as the disodium salt if sodium hydroxide is present in a sufficiently high amount. For convenience's sake, the term "tartaric acid" is used throughout the description for the acidic form as well as for the tartrate and bitartrate forms.

As mentioned above, the aqueous mixture of tartaric acids with between 55 and 90% by weight being meso-tartaric acid is preferably used for the preparation of an additive for potassium chloride compositions and more preferably for the preparation of an additive for sodium chloride compositions, e.g. to prevent caking (in that case the additive is denoted as a non-caking additive for potassium chloride or sodium chloride). Said non-caking additive is an iron salt of said mixture of tartaric acids. For that purpose, preferably, an aqueous mixture of tartaric acids is used with between 60 and 80% by weight of the tartaric acids being meso-tartaric acid.

The term "potassium chloride composition" as used throughout the description is meant to denominate all compositions of which more than 75% by weight consists of KCl. Preferably, such a composition contains more than 90% by weight of KCl.

The term "sodium chloride composition" as used throughout the description is meant to denominate all compositions of which more than 75% by weight consists of NaCl. Preferably, such a composition contains more than 90% by weight of NaCl. More preferably, it contains more than 92% of NaCl, while a salt of more than 95% by weight NaCl is most preferred. Typically, the salt will contain about 2-3% water. The salt may be rock salt, solar salt, salt obtained by steam evaporation of water from brine, and the like.

In step (ii) of the process according to the present invention, typically a slurry is obtained. This slurry comprises a mixture of tartaric acids with between 55 and 90% by weight of meso-tartaric acid and more preferably with between 60 and 80% by weight of meso-tartaric acid. More particularly, the liquid phase of said slurry comprises a mixture of tartaric acids of which between 0 and 50% by weight is meso-tartaric acid (weight percentage being based on the total weight of the tartaric acids present in said liquid phase), whereas the solid phase will be predominantly meso-tartaric acid.

Preferably, in a further step water is added to the aqueous mixture, during or after a cooling step (iii). This is particularly preferred if a non-caking additive for sodium chloride is to be made so that a treatment solution (comprising the composition according to the present invention comprising tartaric acid wherein between 55 and 90% by weight, preferably between 60 and 80% by weight, is the meso isomer) for the sodium chloride composition is prepared having the required concentration. An iron salt, which can be a di- or a trivalent iron source, but which is preferably $FeCl_3$, can subsequently be added to said solution (or said solution can be added to a di- or a trivalent iron source, preferably in the form of an aqueous solution) in the desired amount, after which the obtained treatment solution can be sprayed onto a sodium chloride composition. By using the aqueous slurry obtained in step (ii) as such (i.e. the solids and all adhering liquid, without any separation), an easy and quick preparation method of a non-caking additive is obtained. However, as the skilled person will recognize it is also possible to use only part of the adhering liquid together with the solids to make an aqueous mixture comprising a mixture of tartaric acids wherein between 55 and 90% by weight, and preferably between 60 and 80% by weight, is meso-tartaric acid. It is also possible to use part of the solids and all or part of the adhering liquid to make the aqueous mixture according to the present invention.

For the preparation of a non-caking additive, an iron source is added to a mixture of tartaric acids with between 55 and 90% by weight of meso-tartaric acid and more preferably with between 60 and 80% by weight of meso-tartaric acid, in such an amount that the molar ratio between iron and the total amount of tartaric acid in the non-caking additive (i.e. the molar amount of iron divided by the total molar amount of tartaric acid) is preferably between 0.1 and 2, more preferably between 0.3 and 1.

The present invention is further illustrated by the following examples.

EXAMPLES

Example 1a

Via L-Tartaric Acid

In a 200-liter steam heated jacketed vessel 156.6 kg of 50 wt % sodium hydroxide (in water) solution (ex Sigma, analyzed NaOH concentration 49.6 wt %) was mixed with 18.4 kg of demineralized water and 106.1 kg L-tartaric acid (ex Caviro Distillerie, Italy). Neutralization took place to yield a solution containing 48.7 wt % L-tartaric disodium salt, 7.5 wt % free NaOH, and 43.7 wt % water. The mixture was boiled at atmospheric pressure under total reflux and stirring for 24 hours in total. During this period samples were taken and the conversion of L-tartrate to mesotartrate was determined by $^1$H-NMR. Results can be found in Table 1. During the synthesis some of the meso-tartrate reacted further to D-tartrate.

TABLE 1

Relative conversion in time according to Example 1a.

| Time [hours] | Meso-tartaric acid [wt % of total TA] | D + L [wt % of total TA] |
|---|---|---|
| 0 | 0 | 100 |
| 2.0 | 22 | 78 |
| 4.0 | 29 | 71 |
| 5.7 | 33 | 67 |
| 7.7 | 45 | 55 |
| 9.8 | 51 | 49 |
| 11.7 | 54 | 46 |
| 13.7 | 61 | 39 |
| 15.8 | 66 | 34 |
| 17.7 | 70 | 30 |
| 19.7 | 73 | 27 |
| 22.8 | 76 | 24 |
| 24.0 | 77 | 23 |

After approximately 4.0-4.5 hours of boiling, the mixture became hazy and solids were precipitating from the solution. During the rest of the experiment the slurry density was increasing.

Via chiral HPLC the absolute amounts of D-, L-, and meso-tartaric acid were determined (Column used: Chirex 3126 (D)-penicillamine (ligand exchange)) (see Table 2).

HPLC Conditions

Guard column: none

Analytical column: Chirex 3126 (D) 50×4.6 mm ID; $d_p$=5 μm

Mobile phase: Mixture of 90% Eluent A, 10% Eluent B. Filtered and degassed

Eluent A: 1 mM Copper (II) acetate and 0.05 M Ammonium acetate, pH=4.5 (using Acetic acid)

Eluent B: Isopropanol

Separation mode: Isocratic

Flow rate: 2.0 ml/min

Temperature: 50° C.

Injection volume: 2 μl

Detection: UV at 280 nm

TABLE 2

Relative conversion in time according to Example 1a.

| | Expressed as sodium salt form | | | Meso | D + L |
|---|---|---|---|---|---|
| Time [hours] | Meso [wt %] | L [wt %] | D [wt %] | [wt % of total TA] | [wt % of total TA] |
| 2 | 10.6 | 34.5 | 1.1 | 23 | 77 |
| 4 | 14.5 | 30.4 | 2.5 | 31 | 69 |
| 5.8 | 17 | 27.3 | 3.8 | 35 | 65 |
| 7.8 | 22.2 | 20.8 | 5 | 46 | 54 |
| 9.8 | 24.9 | 17.5 | 5.1 | 52 | 48 |
| 11.8 | 26.7 | 16 | 5.3 | 56 | 44 |
| 13.8 | 30.7 | 12.3 | 5.2 | 64 | 36 |
| 15.8 | 33.2 | 10.4 | 4.8 | 69 | 31 |
| 17.8 | 35.2 | 9 | 4.4 | 72 | 28 |
| 19.8 | 36.3 | 7.7 | 4.3 | 75 | 25 |
| 22.9 | 32.7 | 5.5 | 3.4 | 79 | 21 |
| 24 | 38.9 | 6.4 | 3.9 | 79 | 21 |

HPLC results confirm $^1$H-NMR results.

Example 1b

Via D/L-Tartaric Acid

In a 30-liter steam heated jacketed vessel 15.41 kg of 50 wt % of sodium hydroxide (in water) solution (ex Sigma) was mixed with 1.815 kg of demineralized water and 10.592 kg of racemic DL-tartaric acid (ex. Jinzhan, Ninghai organic chemical factory, China). The mixture was boiled under reflux at atmospheric pressure and stirred for 190 hours in total. During this period samples were taken of the reaction mixture and the conversion of DL-tartrate to mesotartrate was determined by $^1$H-NMR (see Table 3).

TABLE 3

Relative conversion in time according to Example 1b.

| Time [hours] | meso [wt % of total TA] | DL [wt % of total TA] |
|---|---|---|
| 0 | 0 | 100 |
| 2 | 8 | 92 |
| 4 | 12 | 88 |
| 24 | 47 | 53 |
| 29 | 56 | 44 |
| 46 | 73 | 27 |
| 70 | 78 | 22 |
| 94 | 83 | 17 |
| 190 | 88 | 12 |

Solids were present during the whole experiment.

Via chiral HPLC the absolute amounts of meso-tartaric acid and DL-tartaric acid were determined. (Column used: Chirex 3126 (D)-penicillamine (ligand exchange)) (see Table 4).

TABLE 4

Relative conversion in time according to Example 1b.

| | Expressed as sodium form | | | meso | DL |
|---|---|---|---|---|---|
| Time [hours] | Meso [wt %] | L [wt %] | D [wt %] | [wt % of total TA] | [wt % of total TA] |
| 2 | 4.1 | 21.2 | 21.3 | 9 | 91 |
| 4 | 6.1 | 20.4 | 20.7 | 13 | 87 |
| 24 | 21.5 | 10.8 | 11.0 | 50 | 50 |
| 29 | 26.0 | 10.2 | 9.9 | 56 | 44 |
| 46 | 31.5 | 5.2 | 5.3 | 75 | 25 |
| 52 | 37.2 | 4.0 | 4.1 | 82 | 18 |
| 70 | 31.2 | 3.8 | 3.9 | 80 | 20 |
| 94 | 35.5 | 3.5 | 3.5 | 84 | 16 |
| 190 | 40.7 | 2.6 | 2.7 | 88 | 12 |

It can be seen that both raw materials (Examples 1a and 1b) lead to the same final product, a tartaric acid mixture containing primarily meso-tartaric acid and some D and L, with D:L ratio approaching 50:50 over time (the thermodynamic equilibrium). L-tartaric acid as starting material gives a faster conversion. Other process parameters such as NaOH concentration influence the conversion rate as well.

Work-up was done by the same method as described in Example 1a.

Comparative Example A

Effect of Higher NaOH Content and Lower Sodium Tartrate Content

Example A (i)

L-Tartaric Acid as Starting Material

In a 1-liter reactor vessel, 606.04 g of NaOH solution (containing 50 wt % of NaOH and 50% of water) was mixed with 414.40 g water and 96.70 g of L-tartaric acid. Upon mixing, a mixture comprising 11.2 wt % of disodium L-tartrate, 22.5 wt % of NaOH and 66.3 wt % of water was obtained. The mixture was heated and was kept at atmospheric boiling conditions under reflux for 26 hours ($T_{boil}$~110° C.), under continuous stirring. A clear solution was obtained. At regular intervals, a sample was taken from the liquid and analysed by $^1$H-NMR for meso-tartaric acid, DL-tartraric acid and acetate content (a distinction between the D and L-enantiomer cannot be made by $^1$H-NMR).

The $^1$H-NMR analysis showed that L-tartaric acid is converted to meso-tartaric acid until a level of about 40 wt % meso (based on the total amount of tartaric acid) is obtained (see Table 5). After that point, prolonged boiling does not result in increased conversion to mesotartrate. However, the amount of byproduct acetate increased with time to about 1 wt %.

After approximately 6 hours of boiling a small amount of solids appeared. 1H-NMR and IR analysis showed this solid to be primarily sodium oxalate, a tartaric acid degradation product.

TABLE 5

Relative conversion in time according to example A(i).

| boiling time (hr) | Meso [wt %] | D + L [wt %] |
|---|---|---|
| 0 | 0 | 100 |
| 1.8 | 2 | 98 |
| 3.8 | 31 | 69 |
| 4.8 | 37 | 63 |
| 5.5 | 39 | 61 |
| 20.2 | 40 | 60 |
| 26.1 | 40 | 60 |

Example A (ii)

A Mixture of Mesotartrate and DL-Tartarate as Starting Material

Prepared were 1,470 g of a mixture containing 11.4 wt % disodium tartrate, (of which 78 wt % was mesotartrate and 22 wt % DL-tartrate), 21.8 wt % NaOH and 66.8 wt % water. For practical reasons, this mixture was prepared from NaOH solution, water and a reaction mixture prepared according to the procedure in Example 1a. This means that the starting mixture is in all respects similar to the starting mixture of example A(i), except for the meso:DL ratio of the disodium tartrate. The mixture was heated and was kept at atmospheric boiling conditions under reflux for 26 hours ($T_{boil}$~110° C.), under continuous stirring. A clear solution was obtained. At regular intervals, a sample was taken from the liquid and analysed by $^1$H-NMR for meso-tartaric acid, DL-tartaric acid and acetate content (a distinction between the D and L-enantiomer cannot be made by NMR).

The $^1$H-NMR analysis showed that meso-tartaric acid is converted to DL-tartaric acid until a level of about 40 wt % meso-tartaric acid (based on the total amount of tartaric acids) is obtained (see Table 6). After approximately 22 hours of boiling an equilibrium is reached. However, the amount of byproduct acetate increased with time to about 1 wt %.

After approximately 6 hours of boiling, a small amount of solids appeared. 1H-NMR and IR analysis showed this solid to be primarily sodium oxalate, a tartaric acid degradation product.

TABLE 6

Relative conversion in time according to example A(ii).

| boiling time (hr) | Meso [wt % of total TA] | D + L [wt % of total TA] |
|---|---|---|
| 0.0 | 77 | 23 |
| 3.0 | 70 | 30 |
| 4.1 | 52 | 48 |
| 5.1 | 43 | 57 |
| 6.1 | 42 | 58 |
| 7.1 | 42 | 58 |
| 22.0 | 40 | 60 |
| 26.0 | 40 | 60 |

For further illustration, the progress of both experiments is shown in FIG. 1. The results of Example A(i) are indicated with solid lines (with —◇— representing the amount of meso-tartaric acid, and —■— representing the combined amounts of D- and L-tartaric acid). The results of Example A(ii) are indicated with dashed lines (with - - ◇ - - representing the amount of meso-tartaric acid, and - - ■ - - representing the combined amounts of D- and L-tartaric acid).

It was found that an equilibrium was reached after about 6 hours with about 40 wt % of meso-tartaric acid and 60 wt % of D- and L-tartaric acid.

Comparative Example B

Effect of a Lower Sodium Tartrate Content

Example B(i)

L-Tartaric Acid as Starting Material

In an experiment similar to Example A(i), 1,616 g of NaOH solution (containing 50 wt % NaOH and 50 wt % water) were mixed with 2,964.5 g water and 759.5 g L-tartaric acid. Upon mixing, the acid was neutralized, leading to a mixture containing 18.4 wt % disodium L-tartrate, 7.5 wt % NaOH and 74.1 wt % water. The mixture was heated and was kept at atmospheric boiling conditions under reflux for 46 hours ($T_{boil}$~110° C.), under continuous stirring. A clear solution was obtained. At regular intervals, a sample was taken from the liquid and analysed by $^1$H-NMR for meso-tartaric acid, DL-tartaric acid and acetate content (a distinction between the D and L-enantiomer cannot be made by NMR).

The $^1$H-NMR analysis showed that L-tartaric acid is converted to meso-tartaric acid until a level of about 35 wt % meso (based on the total amount of tartaric acid) is obtained (see Table 7). After approximately 25 hours of boiling, no increase in conversion towards meso-tartaric acid is observed anymore. The amount of byproduct acetate increased with time to about 0.2 wt %.

TABLE 7

Relative conversion in time according to example B(i).

| boiling time (hr) | Meso [wt % of total TA] | D + L [wt % of total TA] |
| --- | --- | --- |
| 0.0 | 0 | 100 |
| 1.1 | 6 | 94 |
| 3.1 | 13 | 86 |
| 5.1 | 19 | 81 |
| 6.8 | 23 | 77 |
| 21.5 | 33 | 67 |
| 25.5 | 33 | 67 |
| 30.8 | 33 | 67 |
| 45.9 | 35 | 65 |

Example B(ii)

A Mixture of Mesotartrate and DL-Tartarate as Starting Material

Prepared were 6.30 kg of a mixture containing 18.6 wt % disodium tartrate, (of which 78% mesotartrate and 22% DL-tartrate), 7.6 wt % NaOH and 73.7 wt % water. For practical reasons, this mixture was prepared from NaOH solution (50% NaOH in 50 wt % water), water and a reaction mixture prepared according to the procedure in Example 1a. The starting mixture is in all respects similar to the starting mixture of Example B[i], except for the meso/DL isomer ratio in the tartaric acid. The mixture was heated and was kept at atmospheric boiling conditions under reflux for 53 hours ($T_{boil}$~110° C.), under continuous stirring. A clear solution was obtained. At regular intervals, a sample was taken from the liquid and analyzed by $^1$H-NMR for meso-tartaric acid, DL-tartaric acid and acetate content (a distinction between the D and L-enantiomer cannot be made by NMR).

The $^1$H-NMR analysis showed that meso-tartaric acid is converted to DL-tartaric acid until a level of about 34 wt % meso-tartaric acid (based on the total amount of tartaric acid) is obtained (see Table 8). After approximately 31 hours, an equilibrium is reached. However, the amount of byproduct acetate increased with time to about 0.4 wt % after 46 hrs.

TABLE 8

Relative conversion in time according to example B(ii).

| boiling time (hr) | Meso [wt % of total TA] | D + L [wt % of total TA] |
| --- | --- | --- |
| 0.0 | 78 | 22 |
| 1.5 | 73 | 27 |
| 3.0 | 70 | 30 |
| 4.5 | 65 | 35 |
| 6.8 | 60 | 40 |
| 22.6 | 38 | 62 |
| 26.3 | 36 | 64 |
| 28.3 | 35 | 65 |
| 31.6 | 34 | 66 |
| 46.7 | 32 | 68 |
| 52.5 | 34 | 66 |

For further illustration, the experiments from Example B(i) and B(ii) are shown in FIG. 2. The results of Example B(i) are indicated with solid lines (with —◊— representing the amount of meso-tartaric acid, and —■— representing the combined amounts of D- and L-tartaric acid). The results of Example B(ii) are indicated with dashed lines (with - - ◊ - - representing the amount of meso-tartaric acid, and - - ■ - - representing the combined amounts of D- and L-tartaric acid).

At this lower NaOH content, the equilibrium is located at about 34 wt % meso-tartaric acid and 66 wt % DL-tartaric acid (of the total amount of tartaric acid); the formation of the byproduct acetate is considerably lower than in Example A. The reaction is slower.

The invention claimed is:

1. A process for the preparation of a composition comprising tartaric acid wherein between 55 and 90% by weight of the tartaric acid is meso-tartaric acid, comprising the steps of
   (i) preparing an aqueous mixture comprising between 35 and 65% by weight of a di-alkali metal salt of L-tartaric acid, a di-alkali metal salt of D-tartaric acid, a mixture of di-alkali metal salts of L-tartaric acid and D-tartaric acid, or a mixture di-alkali metal salts of L-tartaric acid, D-tartaric acid and meso-tartaric acid having less than 50% by weight of meso-tartaric acid, and between 1.3 and 20.6 mol % of a free alkali metal or alkaline earth metal hydroxide, and
   (ii) stirring and heating the aqueous mixture of step (i) to a temperature of between 100° C. and its boiling point until between 55 and 90% by weight of tartaric acid has been converted to meso-tartaric acid.

2. The process according to claim 1, further comprising a step (iii) wherein the aqueous mixture of step (ii) is cooled.

3. The process according to claim 1, wherein the alkali metal in the tartaric acid salt comprises sodium and wherein the alkali metal hydroxide comprises sodium hydroxide.

4. The process according to claim 1, wherein in step (i) L-tartaric acid disodium salt is used.

5. The process according to claim 1, wherein the process is carried out at atmospheric pressure.

6. The process according to claim 1, wherein the aqueous mixture is stirred and heated in step (ii) for between 3 and 200 hours.

7. The process according to claim 1, wherein the aqueous mixture prepared in step (i) comprises between 40 and 60% by weight of a di-alkali metal salt of L-tartaric acid, a di-alkali metal salt of D-tartaric acid, a mixture of di-alkali metal salts of L-tartaric acid and D-tartaric acid, or a mixture of di-alkali metal salts of L-tartaric acid, D-tartaric acid, and meso-tartaric acid having less than 50% by weight of meso-tartaric acid.

8. The process according to claim 1, wherein the aqueous mixture prepared in step (i) comprises between 2.73 and 12.67 mol % of a free alkali metal or free alkaline earth metal hydroxide.

9. The process according to claim 1, wherein between 60 and 80% by weight of the tartaric acid is meso-tartaric acid.

10. A process for the preparation of a non-caking additive for a sodium chloride composition or a potassium chloride composition comprising admixing into a non-caking additive a composition comprising tartaric acid, wherein between 55 and 90% by weight of the tartaric acid is meso-tartaric acid, which is obtained by the process according to claim 1.

11. The process according to claim 10 wherein the non-caking additive is an iron complex of tartaric acid, with between 55 and 90% by weight of said tartaric acid being meso-tartaric acid.

12. The process according to claim 11 wherein the non-caking additive is an iron complex of tartaric acid, with between 60 and 80% by weight of said tartaric acid being meso-tartaric acid.

13. The process according to claim 2, wherein the alkali metal in the tartaric acid salt comprises sodium and wherein the alkali metal hydroxide comprises sodium hydroxide.

14. The process according to claim 2, wherein in step (i) L-tartaric acid disodium salt is used.

15. The process according to claim 2, wherein the process is carried out at atmospheric pressure.

16. The process according to claim 2, wherein the aqueous mixture is stirred and heated in step (ii) for between 3 and 200 hours.

17. The process according to claim 2, wherein the aqueous mixture prepared in step (i) comprises between 40 and 60% by weight of a di-alkali metal salt of L-tartaric acid, a di-alkali metal salt of D-tartaric acid, a mixture of di-alkali metal salts of L-tartaric acid and D-tartaric acid, or a mixture of di-alkali metal salts of L-tartaric acid, D-tartaric acid and meso-tartaric acid having less than 50% by weight of meso-tartaric acid.

18. The process according to claim 2, wherein the aqueous mixture prepared in step (i) comprises between 2.73 and 12.67 mol % of a free alkali metal or free alkaline earth metal hydroxide.

19. The process according to claim 2, wherein between 60 and 80% by weight of the tartaric acid is meso-tartaric acid.

20. The process according to claim 10, wherein the composition comprising tartaric acid, wherein between 55 and 90% by weight of the tartaric acid is meso-tartaric acid, is obtained by the process according to claim 2.

21. A process for the preparation of a composition comprising tartaric acid wherein between 55 and 90% by weight of the tartaric acid is meso-tartaric acid, comprising the steps of
  (i) preparing an aqueous mixture comprising between 35 and 65% by weight of a di-alkali metal salt of L-tartaric acid, a di-alkali metal salt of D-tartaric acid, a mixture of di-alkali metal salts of L-tartaric acid and D-tartaric acid, or a mixture di-alkali metal salts of L-tartaric acid, D-tartaric acid and meso-tartaric acid having less than 50% by weight of meso-tartaric acid, and between 2 and 15% by weight of free sodium hydroxide, and
  (ii) stirring and heating the aqueous mixture of step (i) to a temperature of between 100° C. and its boiling point until between 55 and 90% by weight of tartaric acid has been converted to meso-tartaric acid.

* * * * *